(12) United States Patent
Irvin et al.

(10) Patent No.: US 9,051,401 B1
(45) Date of Patent: *Jun. 9, 2015

(54) BIS(THIENYL)ISOPYRAZOLES AND PROCESS FOR PREPARING AND METHOD FOR USING BIS(THIENYL)ISOPYRAZOLES

(71) Applicant: The United States of America, as represented by the Secretary of the Navy, Washington, DC (US)

(72) Inventors: David J. Irvin, San Marcos, TX (US); Jennifer A. Irvin, San Marcos, TX (US); John D. Stenger-Smith, Ridgecrest, CA (US); David L. Witker, Bay City, MI (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/171,313

(22) Filed: Feb. 3, 2014

Related U.S. Application Data

(60) Division of application No. 13/412,789, filed on Mar. 6, 2012, now Pat. No. 8,680,292, which is a division of application No. 12/858,993, filed on Aug. 18, 2010, now Pat. No. 8,183,390, which is a continuation of application No. 12/178,972, filed on Jul. 24, 2008, now Pat. No. 7,829,660, which is a continuation of application No. 11/645,257, filed on Nov. 25, 2006, now Pat. No. 7,456,295.

(51) Int. Cl.
  *C25B 3/00* (2006.01)
  *C08F 128/06* (2006.01)

(52) U.S. Cl.
  CPC .................... *C08F 128/06* (2013.01)

(58) Field of Classification Search
  CPC ........................................................ C25B 3/00
  See application file for complete search history.

(56) References Cited

U.S. PATENT DOCUMENTS

| | | | |
|---|---|---|---|
| 4,206,213 A | 6/1980 | Kleeman et al. | |
| 6,965,509 B2 | 11/2005 | Reynolds et al. | |
| 7,167,353 B2 | 1/2007 | Yuyama et al. | |
| 7,456,295 B1 | 11/2008 | Irvin et al. | |
| 7,608,179 B1 * | 10/2009 | Irvin et al. | 205/419 |
| 8,183,390 B1 | 5/2012 | Irvin et al. | |
| 8,427,812 B1 | 4/2013 | Stenger-Smith et al. | |
| 2008/0192407 A1 | 8/2008 | Lu et al. | |
| 2010/0142122 A1 | 6/2010 | Tanaka | |
| 2010/0172011 A1 | 7/2010 | Piroux et al. | |
| 2011/0045357 A1 | 2/2011 | Sailto et al. | |

OTHER PUBLICATIONS

U.S. Appl. No. 12/878,744, Stenger-Smith, et al.
U.S. Appl. No. 13/412,789, Irvin, et al.
U.S. Appl. No. 13/848,172, Stenger-Smith, et al.
U.S. Appl. No. 13/412,789, Stenger-Smith, et al.
Stenger-Smith, et al, J. of the electrochemical society, 149(8) A973-A977 (2002).
Pringle, et al. Electrochemical synthesis of polypyrrole in ionic liquids, Polymer 45 (2004) 1447-1453.
Pringle, et al. The influence of the monomer and the ionic liquid on the electrochemical preparation of potythiophene. Polymer 46 (2005) 2047-2058.
Pringle, et al. Solid state NMR analysis of polypyrrole grown in a phosphonium ionic liquid, Synthetic Metals 155 (2005) 684-689.
Irvin, et al, Polymer preprints 2007, 48(2) 150.
Witker, et al J. of the electrochemical society, 154(4) G95-G98 (2007).
Stenger-Smith et al, J. of the electrochemical society, 157 A298-A304 (2010).

* cited by examiner

*Primary Examiner* — Kamal Saeed
(74) *Attorney, Agent, or Firm* — Charlene A. Haley

(57) ABSTRACT

A synthesis of a new pyrazole-containing monomer by means of an easily implemented two-step process. This monomer can be electropolymerized to yield a stable n-doping polymer that may easily be electrochemically characterized. It is demonstrated that the electrochemical behavior of the polymer films produced is dependent upon the conditions applied during electrodeposition. Films deposited by cycling only at relatively positive potentials (0 to 2000 mV) show less intense n-doping responses than those films obtained by scanning the applied potential throughout a wider range (−2000 mV to 2000 mV).

9 Claims, 25 Drawing Sheets

BIS(THIENYL)ISOPYRAZOLES AND PROCESS FOR PREPARING AND METHOD FOR USING BIS(THIENYL)ISOPYRAZOLES

CROSS-REFERENCE TO RELATED APPLICATIONS

This is a divisional application claiming the benefit of application Ser. No. 13/412,789 filed on Mar. 6, 2012, which is a divisional application of Ser. No. 12/858,993 filed on Aug. 8, 2010 which is a continuation-in-part, application of parent application Ser. No, 12/178,972 filed on Jul. 24, 2008, which is a continuation of parent application Ser. No. 11/645, 257 filed Nov. 25, 2008 which is now U.S. patent application Ser. No. 7,456,295, which is the parent of divisional patent application Ser. No. 12/178,947 filed Jul. 24, 2008 which is now U.S. Pat. No. 7,608,179, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to processes for preparing bis(thienyl)isopyrazoles via condensation and to methods for using bis(thienyl)isopyrazoles.

BACKGROUND OF THE INVENTION

Electroactive polymers can generally be switched between two or more stable oxidation states, giving rise to changes in properties including conductivity, color, volume, and transmissivity. [G. Inzelt, M. Pineri, J. W. Schultze, and M. A. Vorotyntsev, *Electrochim Acta*, 45, 2403 (2000)]. Electroactive polymers which have been oxidized from a neutral state are said to be p-doped, by analogy to semiconductor terminology. Likewise, polymers that have been reduced from a neutral state are said to be n-doped. Owing to the inherent stability of carbocations, p-dopable materials are quite well known and have been thoroughly documented. [G. Inzelt, M. Pineri, J. W. Schultze, and M. A. Vorotyntsev, *Electrochim Acta*, 45, 2403 (2000); J. Jagur-Grodzinski, *Polym Adv. Tech*, 13, 615 (2002); and, J. W. Schultze and H. Karabulut, *Electrochim Acta*, 50 1739 (2005)]. However, stable n-doped polymers have heretofore been unreported. [D. M. de Leeuw, M. M. J. Simenon, A. R. Brown, and R. E. F. Einerhand, *Synth. Met.*, 87. 53 (1997); K. Wilbourn and R. W. Murray, *Macromolecules*, 21, 89 (1988); and, M. Quinto, S. A. Jenekhe, and A. J. Bard, *Chem. Mater.*, 13, 2824 (2001)]. Such n-doped polymers would be desirable for the same reasons that p-doped polymers have been desired and prepared, as well as for use in applications such as batteries and supercapacitors, for example, [A. Rudge, J. Davey, I. Raistrick, S. Gottesfield, and J. P. Ferraris, *J. Power Sources*, 47, 89 (1994)]. The instability of n-doping conjugated polymers is most likely due to the highly reactive nature of carbanions. [D. M. de Leeuw, M. M. J. Simenon, A. R. Brown, and R. E. F. Einerhand, *Synth. Met.*, 87, 53 (1997)].

One approach being explored to obtain stable n-doping polymers is the synthesis of donor-acceptor materials. [A. Berlin, G. Zotti, S. Zecchin, G. Schiavon, B. Vercelli, and A. Zanelli, *Chem. Mater.*, 16, 3667 (2004); D. J. Irvin, C. J. DuBois, and J. R. Reynolds, *Chem Comm*, 2121 (1999); P. J. Skabara, I. M. Serebryakov, I. F. Perepichka, N. S. Sariciftci, H. Neugebauer, and A. Cravino, *Macromolecules*, 34, 2232 (2001); and, H-F. Lu. H. S. O. Chan, and S-C. Ng, *Macromolecules*, 36, 1543 (2003)]. In a donor-acceptor type of system, the polymer HOMO (highest occupied molecular orbital) is enemetically similar to the relatively high-energy HOMO of the donor material, while the polymer LUMO (lowest unoccupied molecular orbital) is energetically similar to the relatively low-energy LUMO of the acceptor. This type of electronic architecture leads to a small HOMO-LUMO gap in the polymers and consequently to a low-lying polymer LUMO suitable for accepting charge.

The electron-poor functionality of the acceptor groups can be obtained in at least two ways. In the most common approach, electron-withdrawing substituents such as nitro- or fluoro-groups, for example, are incorporated pendant to the main chain of the polymer. [D. J. Irvin, C. J. DuBois, and J. R. Reynolds, *Chem Comm* 2121 (1999); and, P. J. Skabara, I. M. Serebryakov, I. F. Perepichka. N. S. Sariciftci, H. Neugebauer, and A. Cravino, *Macromolecules*, 34. 2232 (2001)]. While this method can yield electron-deficient monomer units and ultimately electron-deficient polymers, it is likely that the substituents act as charge traps, hindering electron mobility.

Electron mobility might be improved, without the aid of pendant groups, by incorporation of functional groups that are themselves intrinsically electron-deficient such as the high nitrogen heterocycles. Typically, as the number of imine-type nitrogens replacing carbon in a given aromatic ring increases, so too does that ring's electron affinity. [G. Brocks and A. Tol, *Synth. Met.*, 101, 516 (1999)].Empirically, the higher the electron affinity of the polymer, the more stable the polymer will he in the n-doped state. [A. P. Kulkarni, C. J. Tonzola, A. Babel, and S. A. Jenekhe, *Chem. Mater.* 16, 4556, (2004)]. Incorporation of these high nitrogen heterocycles into conjugated polymers should result in n-dopable polymers with good electron mobility. Limited research into this type of donor-acceptor polymer has been conducted by others. [A. Berlin. G. Zotti. S. Zecchin, G. Schiavon, B. Vercelli, and A. Zanelli, *Chem. Mater.*, 16, 3667 (2004); and, H-F. Lu, H. S. O. Chan. and S-C. Ng, *Macromolecules*, 36, 1543 (2003)]. The present invention discloses a new stable n-doping donor-acceptor polymer.

Figure 1A:
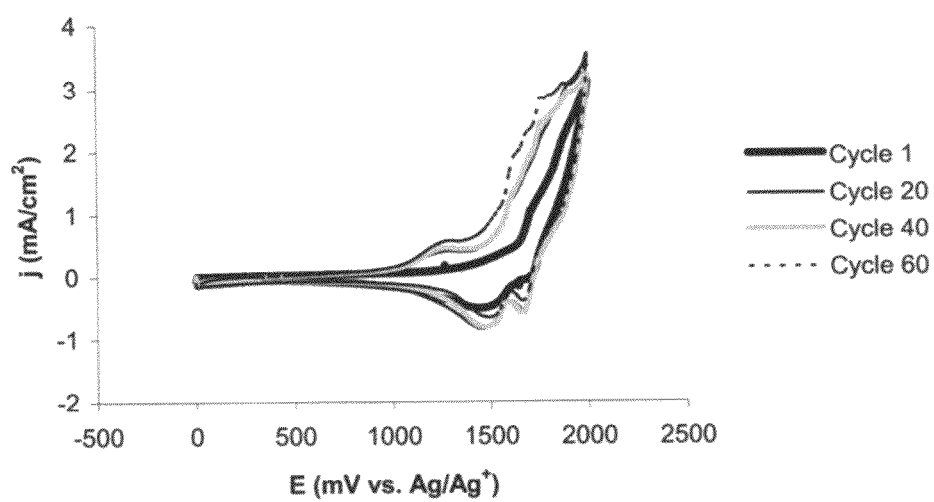
FIGS. 1a-1e are Voltammograms generated by repeated cycling of applied potential at 30 mV/s during electropolymerization of DTDMPy, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE INVENTION

A donor-acceptor polymer based on thiophene and isopyrazole has been prepared for use in n-doping applications. Non-polymerizable monomer radical cations appear to be the predominant oxidation product, resulting in a need for extended cycling to produce adequate quantities of polymer for characterization. Cycling to reductive potentials during oxidative polymerization was necessary to produce a polymer film capable of n-doping, likely resulting from a need to establish pathways for cation migration. The electrochemical behavior of the polymer films produced is strongly dependent upon the conditions applied during electrodeposition. The neutral polymer undergoes oxidation to the p-doped form at ca. 2000 mV vs. Ag/Ag$^+$ and reduces back to neutral at ca. 0 mV. Conversion of the neutral polymer to its n-doped form involves reductions at −700 and −1300 mV, with re-oxidation at −800 and −200 mV to return to the neutral form of the polymer.

As the electron-rich portion of the polymer we have chosen thiophene units, while we have chosen the isopyrazole ring as the electron deficient portion. The isopyrazole group provides high electron affinity and ease of functionalization. [G. Brocks and A. Tol, *Synth. Met.*, 101, 516 (1999)].

Experimental

Dimethyl malonyl chloride, n-butyllithium (2.5 M in hexanes, zinc chloride (1.0 M in diethyl ether), 2-bromothiophene, and palladium (II) chloride were purchased from Aldrich and used as received. Tetrakis-(triphenylphosphine)palladium (0), also commonly written Pd(PPh$_3$)$_4$, was synthesized by reduction of PdCl$_2$ with hydrazine in the presence of triphenylphosphine, also commonly written PPh$_3$.

All electrochemical experiments were performed in a nitrogen atmosphere drybox using a PARSTAT model 2217 potentiostat. Acetonitrile was dried by distillation from calcium hydride. Propylene carbonate was dried by distillation from calcium oxide. Tetramethylammonium tetrafluoroborate (TMABF$_4$) was recrystallized twice from methanol/water. The electrolyte was then dried in a vacuum oven at 100° C. for twenty-four hours before use. Electropolymerizations were conducted with a 10 mM solution of monomer in 100 mM TMABF$_4$/acetonitrile. The working, auxiliary, and reference electrodes were a platinum button (diameter=1.6 mm; area 0.02 cm$^2$), a platinum flag, and a non-aqueous Ag/Ag$^+$ reference electrode, respectively. The potential of the Ag/Ag$^+$ reference electrode was calibrated using the ferrocene/ferrocinium couple. The reduction potential of the couple was found to be 97 mV vs. the reference electrode. All potentials reported herein are relative to the Ag/Ag$^+$ reference electrode. Cycling of the polymer films was accomplished using monomer-free 100 mM TMABF$_4$ in propylene carbonate as the electrolyte system.

Example 1

Synthesis of
1,3-Dithien-2-yl-2,2-dimethylpropane-1,3-dione (DMDTPy).

2-bromothiophene (12.4 mL, 32.0 mmol) was added to 500 mL dry diethyl ether. Then n-butyl lithium (2.5 M in hexanes, 50.8 mL, 127.2 mmol) was added and the mixture was stirred for sixty minutes. After this time, ZnCl$_2$ (1.0 M in ether, 127.2 mL, 127.2 mmol) was added slowly, giving a white precipitate. Next, the reaction mixture was allowed to slowly warm to room temperature and was then refluxed for four hours. Following the reflux period, the reaction mixture was cooled to room temperature and Pd(PPh$^3$)$_4$ (1.85 g, 1.6 mmol) was added followed by the slow addition of dimethyl malonyl chloride (2.0 mL, 15.1 mmol). After completion of the additions, the reaction mixture was brought to reflux and stirred overnight.

After this time, the reaction mixture was poured into 500 mL saturated aqueous sodium bicarbonate. The two-phase mixture was filtered and separated. The organic phase was washed with brine and dried over sodium sulfate. The solvent was removed by rotary evaporation to give a pale orange solid. This solid was dissolved in a minimal amount of acetone and passed through a short plug of silica gel using hexanes as the eluent. Upon removal of the solvent, a pale yellow solid was obtained. This material was recrystallized from hexanes to give pale yellow needles. Yield 3.7 g, 23%. Mp: 159-162° C. $^1$H NMR (CDCl$_3$) δ 7.54 (m, 4 H), 6.99 (dd, 2 H, J=5.0, 4.0 Hz), 1.69 (s, 6 H). IR (KBr pellet, cm$^{-1}$): 3114.4, 3099.0, 2994.1, 2932.5, 1663.3, 1636.2, 1512.9, 1461.1, 1408.0, 1352.6, 1268.8, 1254.0, 1241.7, 1172.6, 1054.3, 965.5, 903.9, 852.1, 825.0, 748.5, 726.3.

Example 2

DMDTPy (1.25 g, 4.7 mmol) and anhydrous hydrazine (1.5 mL, 47 mmol) were combined in 100 mL toluene. The resulting solution was then refluxed for eighteen hours. After this time, the solvent was removed by rotary evaporation and the bright orange solid. remaining was collected and dried in vacuo. Yield 1.21 g, 98%. MP: 153-156° C. $^1$H NMR (CDCl$_3$) δ 7.65 (dd, 2 H, J=3.8, 1.0 Hz), 7.52 (dd, 2 H, J=5.0, 1.0 Hz), 7.17 (dd, J=5.1, 3.8 Hz), 1.70 (s, 6 H). IR (KBr pellet, cm$^{-1}$): 3095.9, 2988.0, 2972.6, 2929.4, 2861.5, 1538.2, 1492.0, 1455.0, 1430.3, 1226.7, 1057.1, 850.4, 835.0, 720.8, 699.3.

Discussion of Examples and Results

Synthesis of the monomer 3,5-Dithien-2-yl-4,4-dimethylpyrazole (DTDMPy) was accomplished using a novel two-step process (Diagram 1). The first step of the process entails coupling a thienylzinc reagent to dimethyl malonyl chloride using a palladium (0) catalyst. The poor ether solubility of the thienylzinc reagent likely contributed heavily to the low yields (23%) attained. The target was easily separated from side products by chromatography and further purified by recrystallization from hexanes. The thienylzine reagent was more soluble in THF than in ether, but the material isolated after the reaction in THF was a complex mixture that could not be readily separated. Infrared spectroscopy of the product showed a sharp, prominent absorbance at 1636 cm$^{-1}$, indicating that conjugated carbonyl groups were present: $^1$H NMR of the product was consistent with the proposed structure.

The second step of the process, a ring-closing reaction with excess hydrazine to provide the pyrazole ring, was accomplished in nearly quantitative yield. This result indicates that the ring-closing step is much more kinetically favorable than is the addition of a second hydrazine to the dione. Infrared spectroscopy of this product showed no trace of the carbonyl vibration observed with the precursor, indicating that the conversion to pyrazole was complete. It will be understood by one skilled in the art that this general reaction scheme may be applied to other ring systems besides thiophene to give a wide array of diarylpyrazole derivatives, including those that are more electron-deficient than DTDMPy. Furthermore, one skilled in the art will be able to incorporate many derivatives beyond the 4,4 dimethylpyrazole. For example, the 4,4 diethylpyrazole could also be synthesized by one skilled in the art.

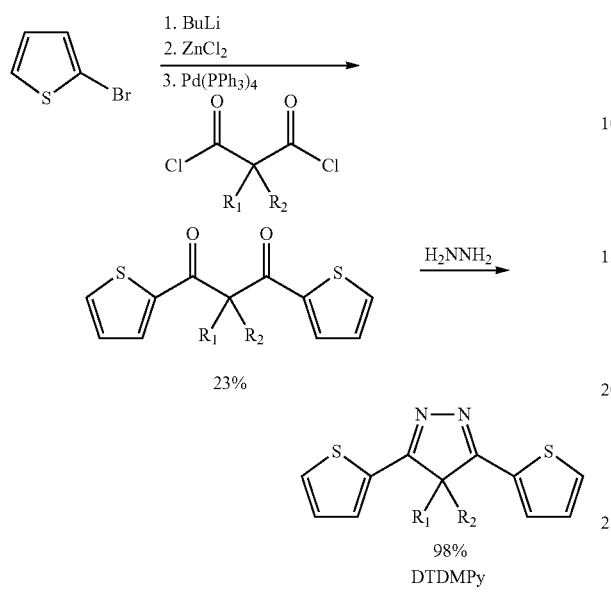

Diagram 1. Synthesis of 3,5-dithien-2-yl-4,4-disubsutited pyrazole (DTDSPy).

This general reaction scheme has been successfully applied to produce other diarylpyrazole derivatives including those substituted at the 4-position of the pyrazole ring with alkyl chains, alkoxy chains, nitro alkanes, halo, cyanoester, mono and/or di-amines, ester, amides, alcohols, suflonates, silyls, and perfluoro alkyl as shown in Diagrams 2-4, as well as to produce diarylpyrazole derivatives having functionalized thiophenes as shown in Diagram 5, where R1 may be hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms: amide including from 1 to 22 carbon atoms; alcohol including from 1 to 22 carbon atoms: ammo; sulphonate groups; silyl; and, perifluoro alky including from 1 to about 22 carbon atoms; R2 selected from the group including of hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulphonate groups; silyl; and, perfluoro alky including from 1 to about 22 carbon atoms; R3 selected from the group including of hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulphonate groups; silyl; and, perfluoro alky including from 1 to about 22 carbon atoms. Such substitutions provide a means to manipulate the electronic and/or solubility properties of the monomer.

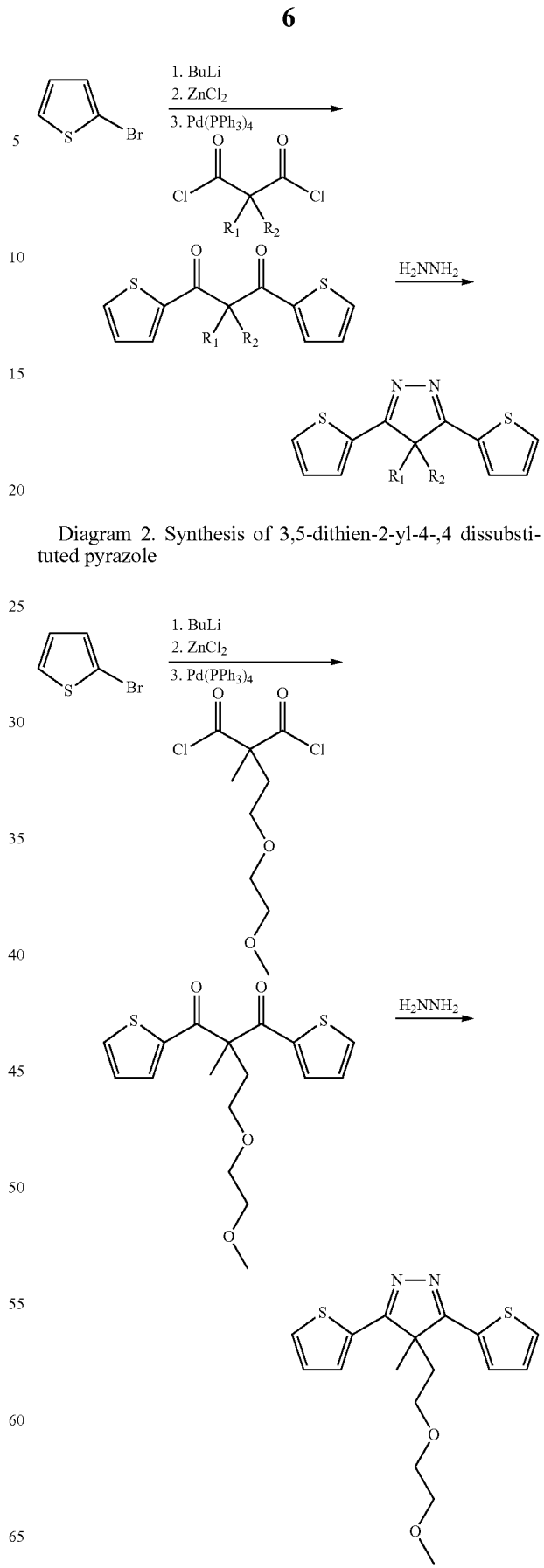

Diagram 2. Synthesis of 3,5-dithien-2-yl-4-,4 dissubstituted pyrazole

Diagram 3. Synthesis of 3,5-dithien-2-yl-4-methyl-4-oligoether-pyrazole.

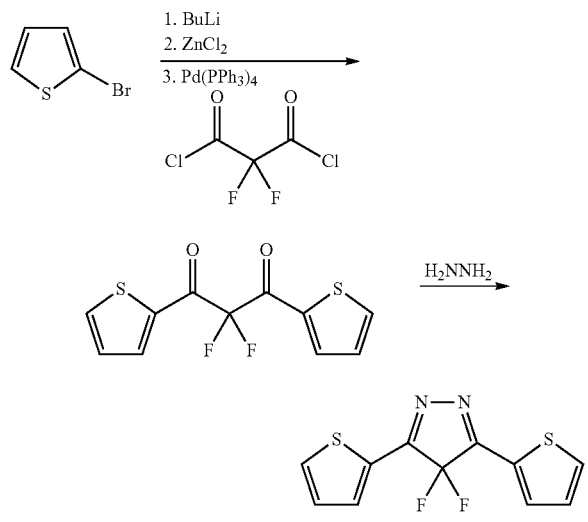

Diagram 4. Synthesis of 3,5-dithien-2-yl-4,4-difluoropyrazole.

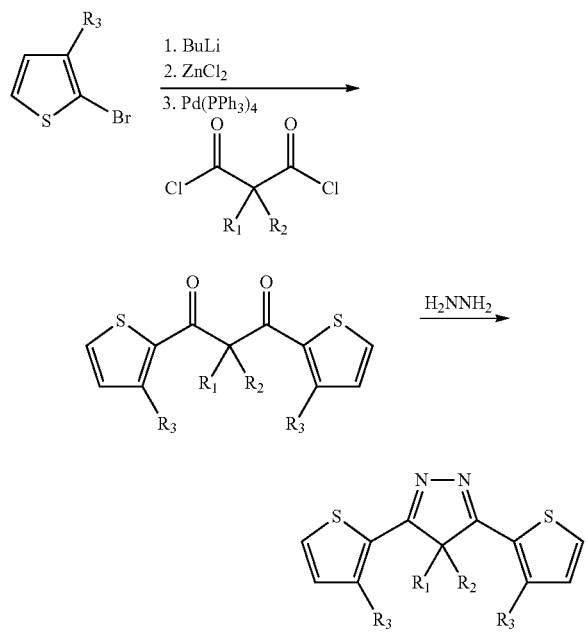

Diagram 5. Synthesis of thiophene substituted 3,5-dithien-3'-organo-2-yl-4,4-disubstitued pyrazole.

A vital consideration in monomer design is the substitution pattern of the pyrazole ring. In order to produce a monomer suitable for electroactive polymers, it is necessary to quaternize the carbon at the 4-position of the pyrazole ring. An unsubstituted pyrazole in this situation has as its major resonance form a protonated amine as part of the ring (Diagram 6). Such an electronic structure of course serves as a conjugation break. In order to exclude this resonance structure, the carbon at the 4-position must he fully substituted. Dimethyl malonyl chloride, a commercially available building block, was used with the expectation that the methyl groups would provide the correct electronic structure for a fully conjugated polymer. In addition, after electropolymerization, the methyl substituents do not impart much solubility to the polymer. Indeed, the polymer films disclosed herein are insoluble in both acetonitrile and propylene carbonate. This property facilitates electrochemical characterization of the films.

Diagram 6. Resonance structures of a 3,5-substituted pyrazole showing a conjugation-breaking major resonance structure and a minor structure giving complete conjugation; 4,4-dimethyl analog with a "locked" electronic structure.

Figure 1B:
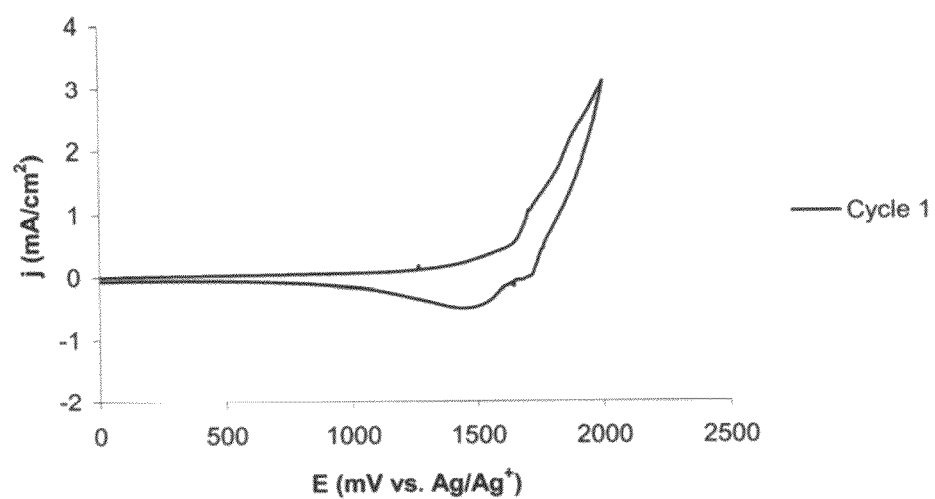
Figure 1C:
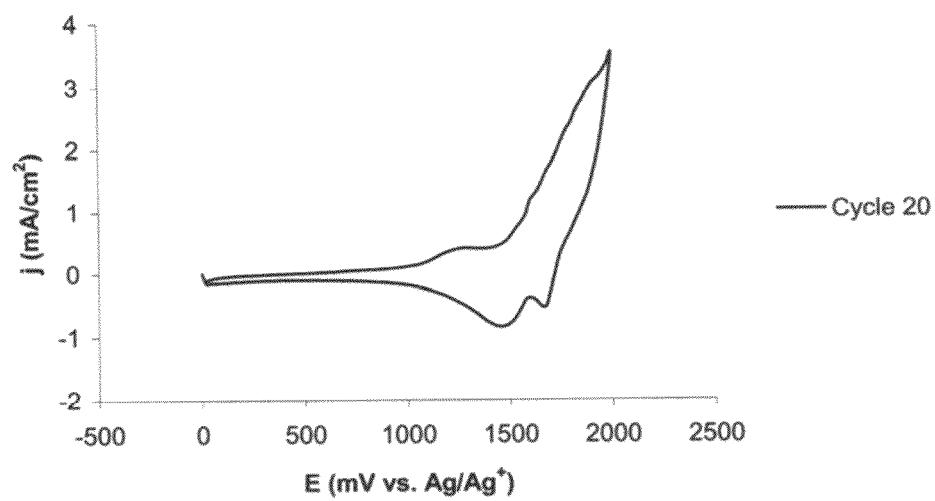
Figure 1D:
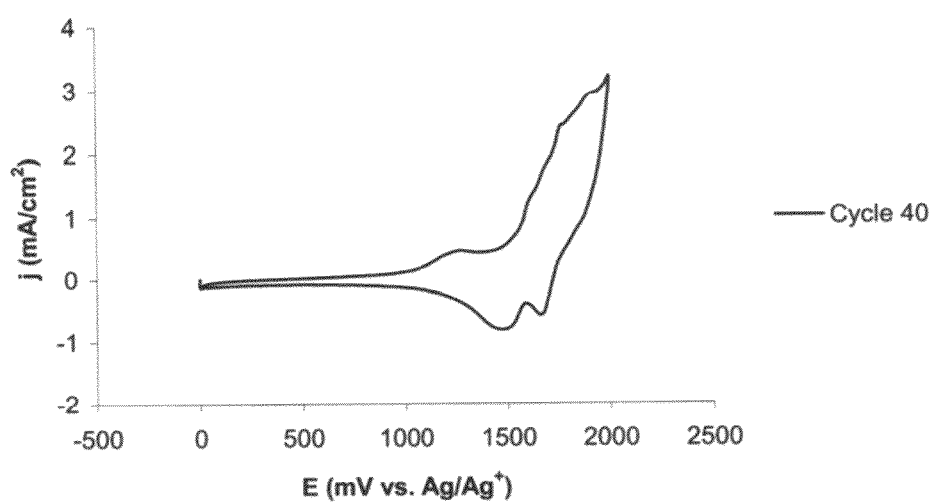
Figure 1E:
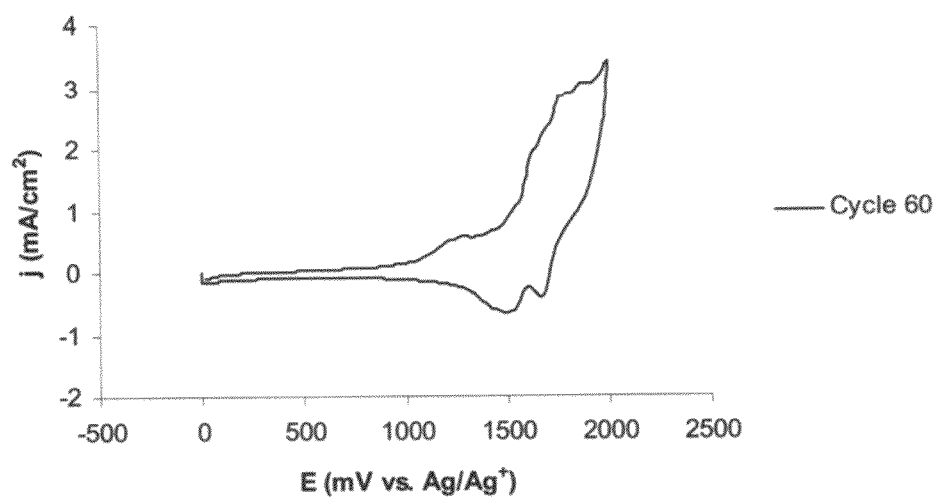

Initial electropolymerizations of DTDMPy were accomplished by cycling the potential applied to a platinum button repeatedly between 0 and 2000 mV versus Ag/Ag$^+$reference. All electrochemical potentials are with respect to this reference. It was necessary to cycle the potential for two hours to produce a film thick enough for electrochemical characterization. This extended cycle time is in contrast to those reported for more electron-rich monomers, such as thiophene derivatives that can be deposited in a relatively shorter time [(G. P. Evans, in *Advances in Electrochemical Science and Engineering*, H. Gerischer and C. W. Tobias, Editors, p. 1. VCH Publishers, Inc., New York, 1990]. With reference to FIGS. 1a-1e, voltammograms generated by repeated cycling of applied potential at 30 mV/s during electropolymerization show monomer oxidation onset at about 1200 mV and peak at about 1800 mV together with a slowly increasing current response centered at about 1200 mV. This increasing current response may be attributed to polymer oxidation. Interestingly, there is no discernable corresponding reduction for the polymer. Instead, reductions at more positive potentials are present which are most likely due to monomer reduction. This suggests that a large portion of the monomer is first oxidized and then reduced without coupling to form polymer. Hence, the polymer reduction response is most probably obscured by the more intense monomer reduction current.

The limited coupling occurring upon monomer oxidation may be explained by considering the effect of the pyrazole ring on the resonance forms of the monomer. As is the case with a monomer such as terthiophene, oxidation gives a radical cation. The radical may he located at the 5-position of a terminal thiophene. thus leading ultimately to 2,5-linked polythiophene (Diagram 7), However, if the radical migrates through the terthiophene monomer, it may he located on the 3- or 4-position of one of the thiophene rings. This electronic arrangement leads to the often-undesirable irregularly linked polymer chains that are not fully conjugated.

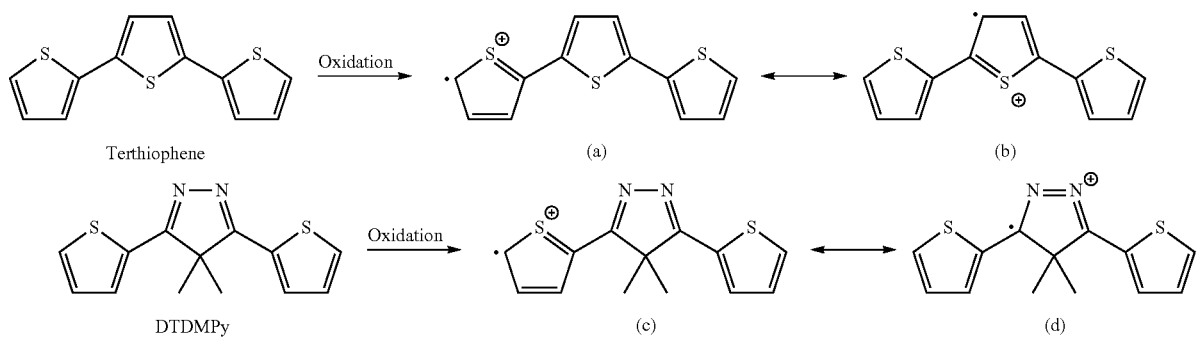

Diagram 7. Oxidation forms of terthiophene and DTDMPy. Oxidation of terthiophene showing structures giving rise to (a) desirable 2,5-linkages and (b) often-undesirable 3,5-linkages; oxidation of DTDMPy showing structures leading to (c) polymer and (d) monomer re-neutralization.

By analogy, DTDMPy may be oxidized, giving a radical cation in which the radical is located upon the 5-position of the terminal thiophene. This configuration or form of course gives rise to the desired polymer. On the other hand, the radical may migrate to the 3-position of the pyrazole ring so that the positive charge resides upon the nitrogen at the 1-position of the ring. In this case, the steric hindrance around the radical center most likely prevents any coupling. As the applied potential becomes more negative, the stabilized radical cations are then reduced without coupling. The more prevalent structure or configuration is the resonance form in which the radical is located at the 3-position of the pyrazole ring and the positive charge is found on the nitrogen, given that the monomer redox couple is much more intense in the voltammograms than are the current responses corresponding to the polymer.

Figure 2A:
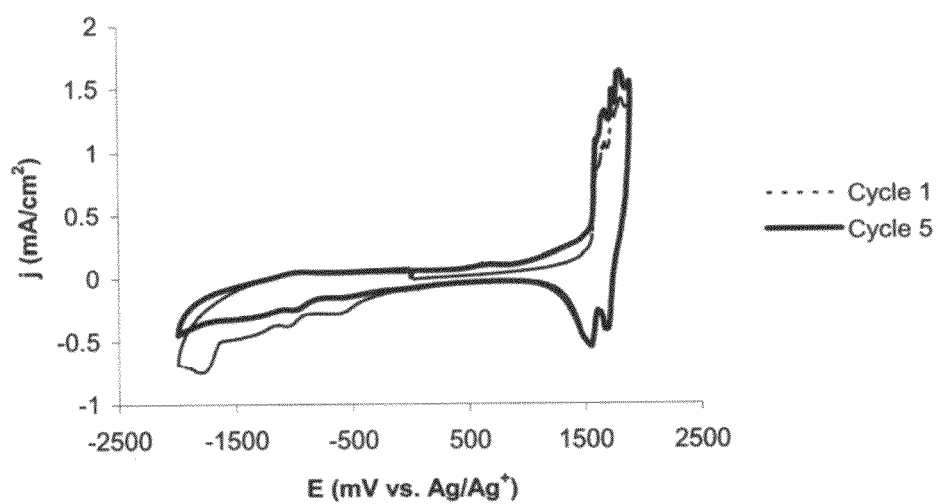
FIGS. 2a-2e is a diagram of redox cycling of poly(DTDMPy) showing prominent p-doping responses and faint n-doping signals, according to embodiments of the invention.
Figure 2B:
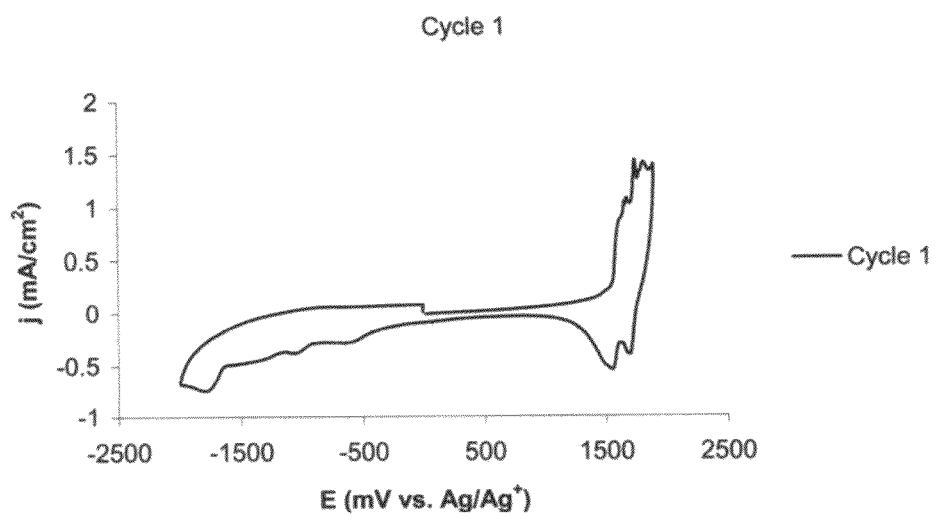
Figure 2C:
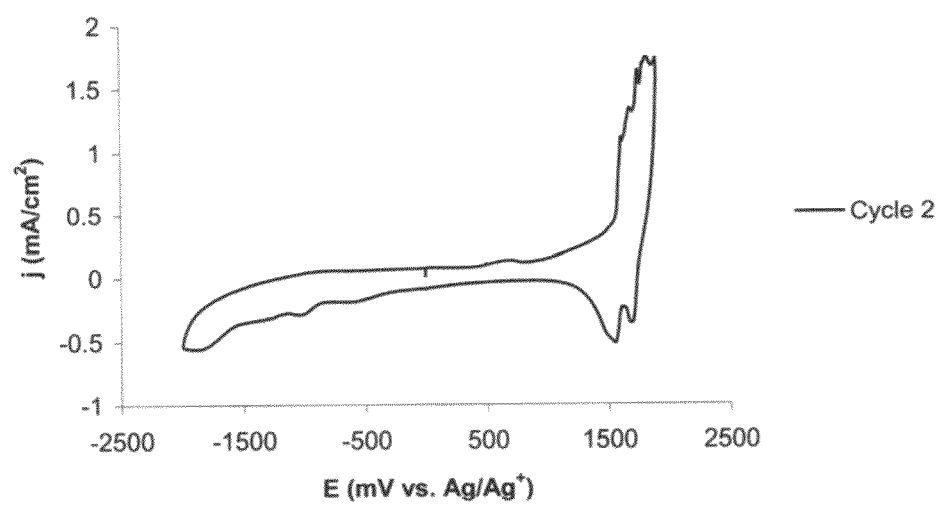
Figure 2D:
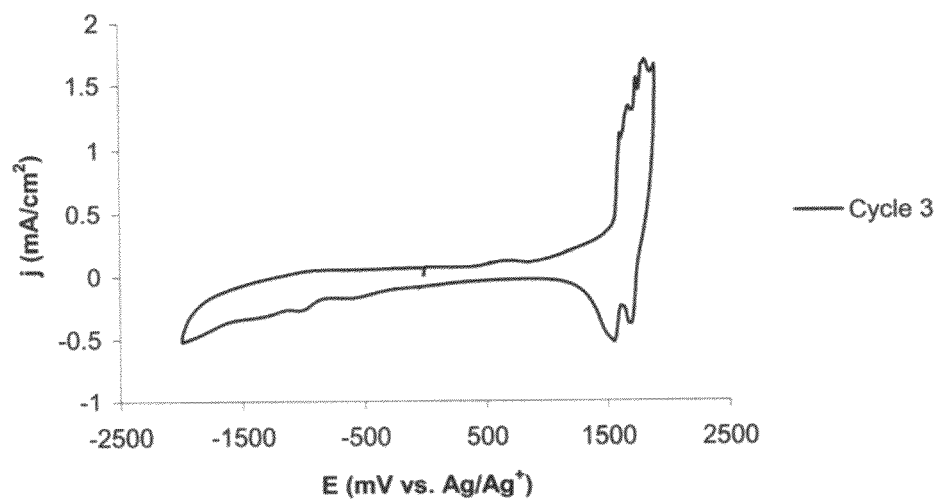
Figure 2E:
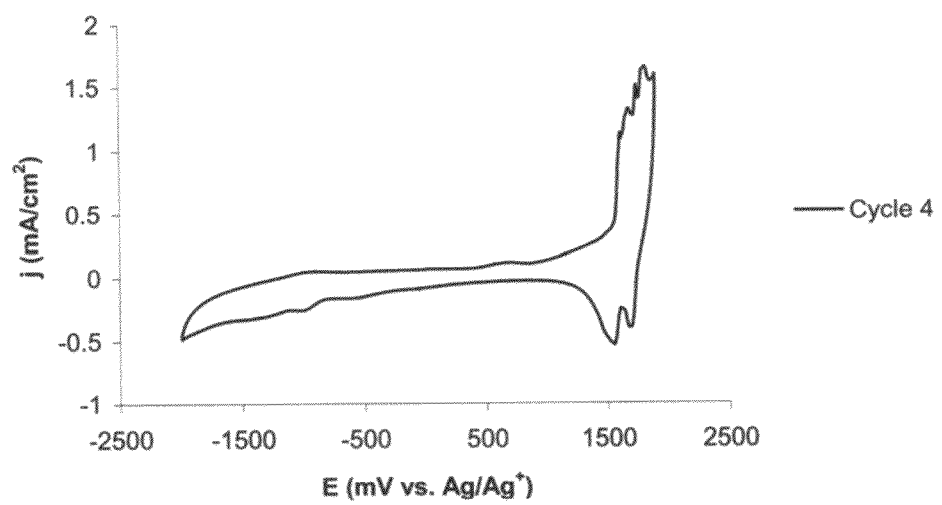

With reference to FIGS. 2a-2e, upon cycling of the polymer film in monomer-free 100 mM $TMABF_4$/propylene carbonate, a redox couple with an onset of about 1500 mV and peak about 1800 mV is readily observed. The rather positive potentials required to oxidize this polymer are most likely a result of the electron-deficient pyrazole units in the polymer backbone. In addition to the p-doping signals, less intense current responses can be observed at more negative potentials, indicating that the polymer is being n-doped. The relative difference in intensity between the p-doping and n-doping regions of the voltammograms are likely a result of the electrodeposition process. As the applied potential is cycled between 0 and 2000 mV to deposit polymer, anions necessarily migrate into the growing polymer film upon oxidation and out of the film upon reneutralization. This process establishes channels for anions to maintain charge balance during post-deposition cycling. Because these anion channels are established during film growth, the process of p-doping proceeds quite well. During polymer reduction, it is likely that cations must be able to freely move into and out of the film. Since the film was not n-doped during deposition, channels for cation migration were not established. Further, because the tetrabutylammonium cations are so much larger than the tetrafluoroborate anions, the anion channels are inadequate for cation transport.

Figure 3A:
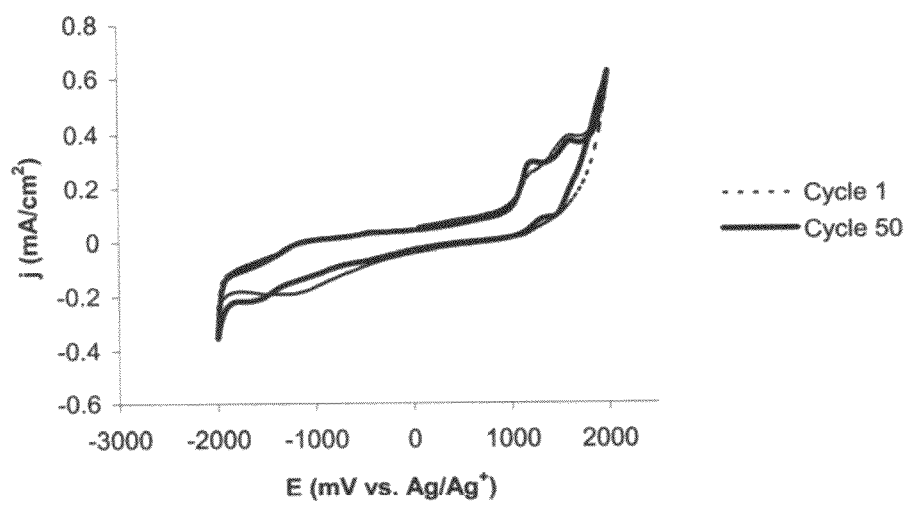
FIGS. 3a-3e is a diagram of electrodeposition of poly (DTDMPy) at 30 mV/s with an expanded potential scan range (2000 to −2000 mV) to include n-doping potentials, according to embodiments of the invention.
Figure 3B:
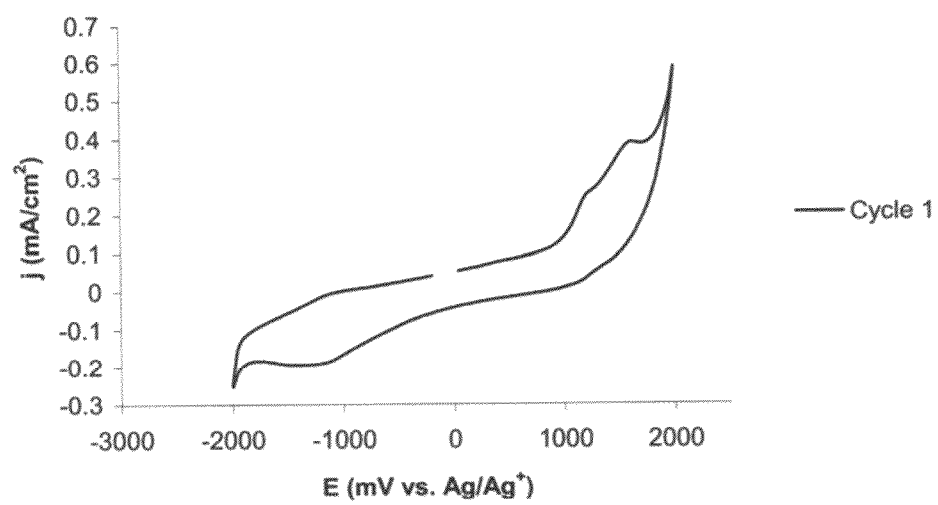
Figure 3C:
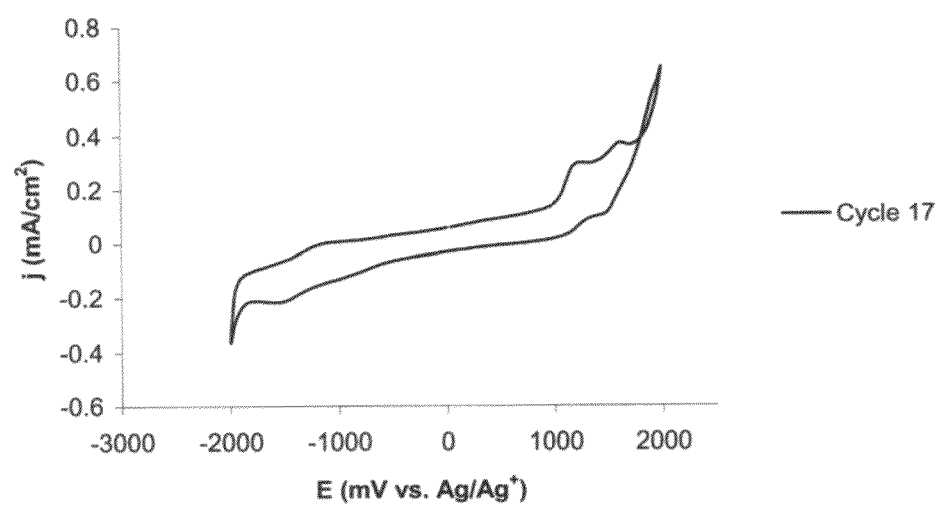
Figure 3D:
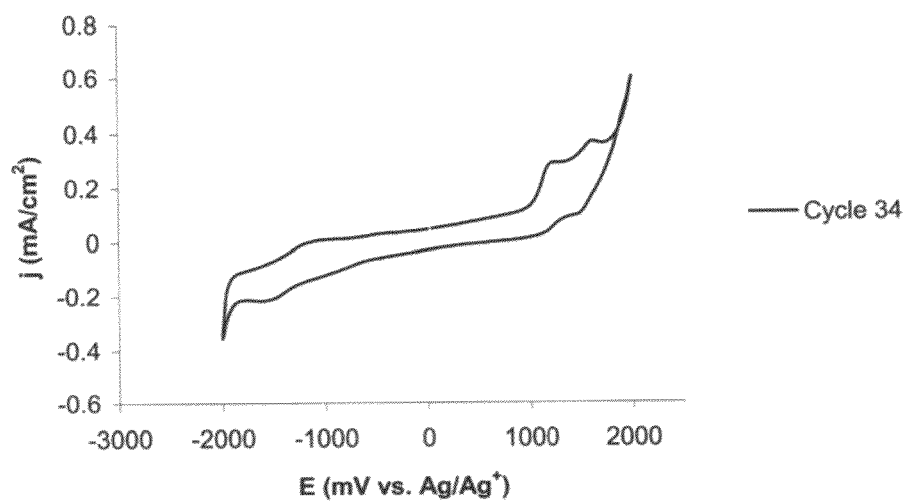
Figure 3E:
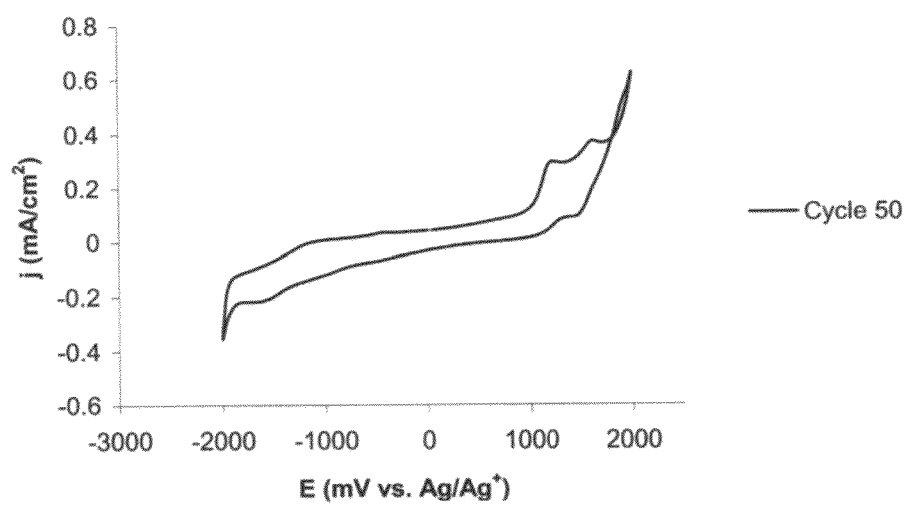

In order to determine the effects of a broader cycling window, a new film was deposited by cycling the applied potential between −2000 and 2000 mV, With reference to FIGS. 3a-3e, as observed previously with electrodeposition scans between 0 and 2000 mV. the oxidative region of the voltammograms show oxidations corresponding to the monomer at about 1500 mV and corresponding to the polymer at roughly 1200 mV. In addition, there is a faint n-doping process that can be discerned at roughly −1200 mV. The voltammograms from this electropolymerization suggest that both anions and cations are moving into and out of the film during the deposition process.

Figure 4A:
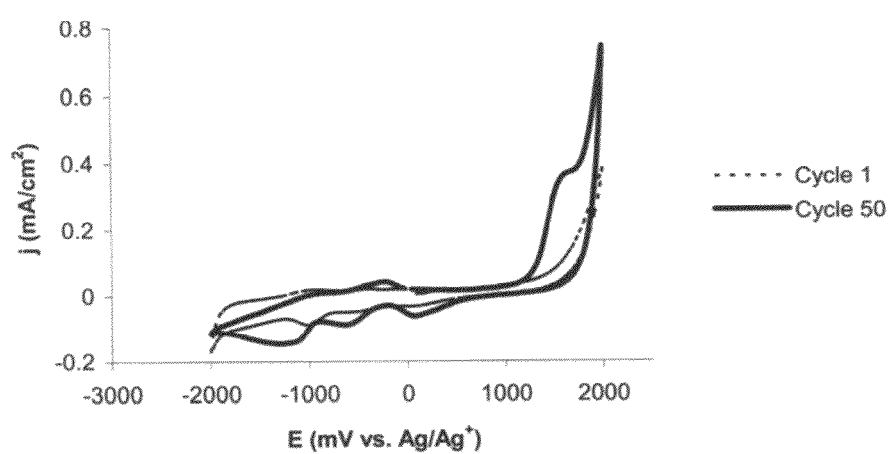
FIGS. 4a-4e is a diagram of redox cycling of poly(DTDMPy) film produced with an expanded potential scan, according to embodiments of the invention.
Figure 4B:
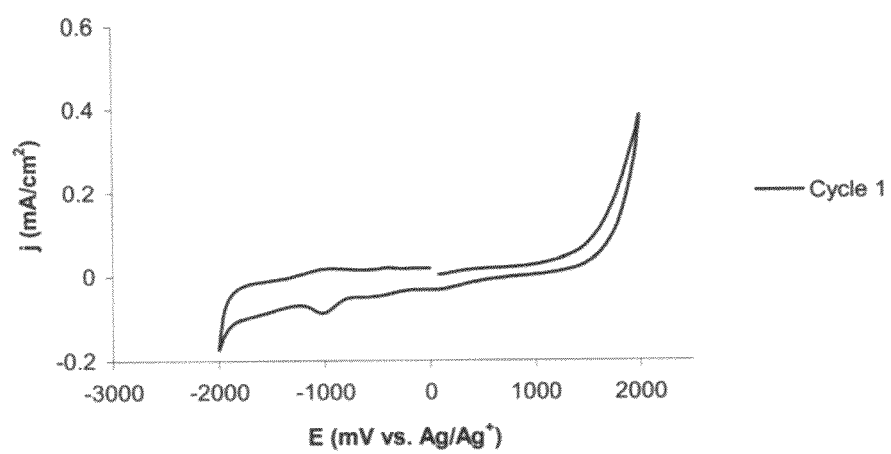
Figure 4C:
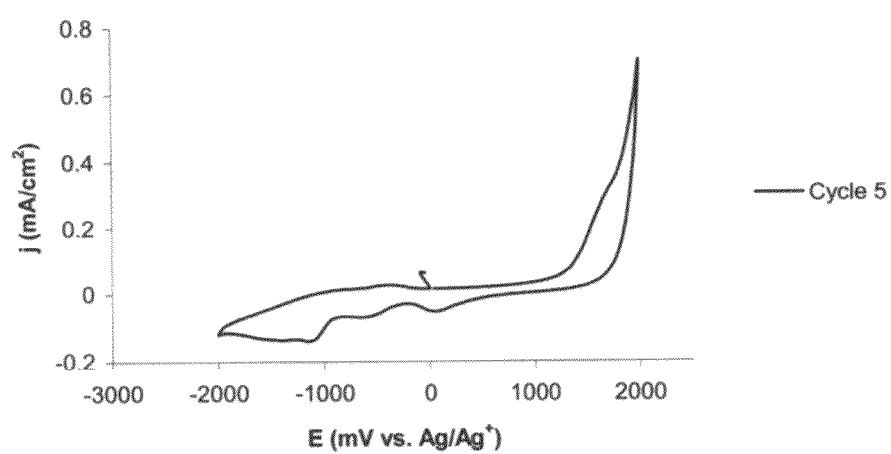
Figure 4D:
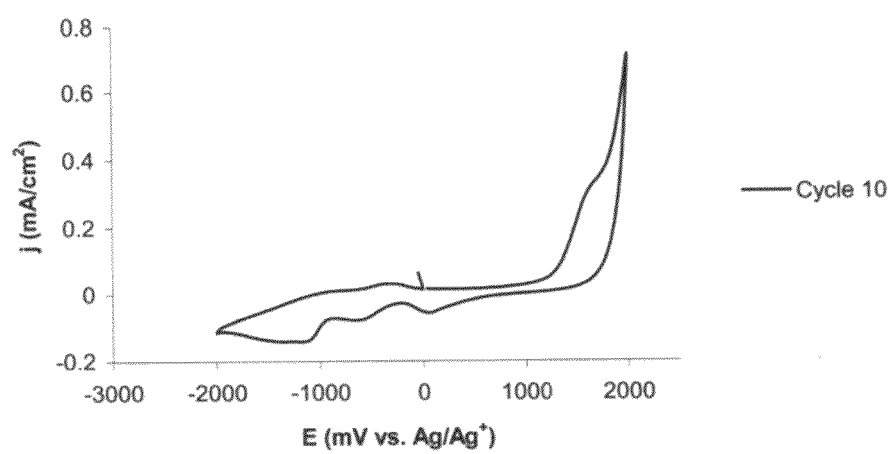
Figure 4E:
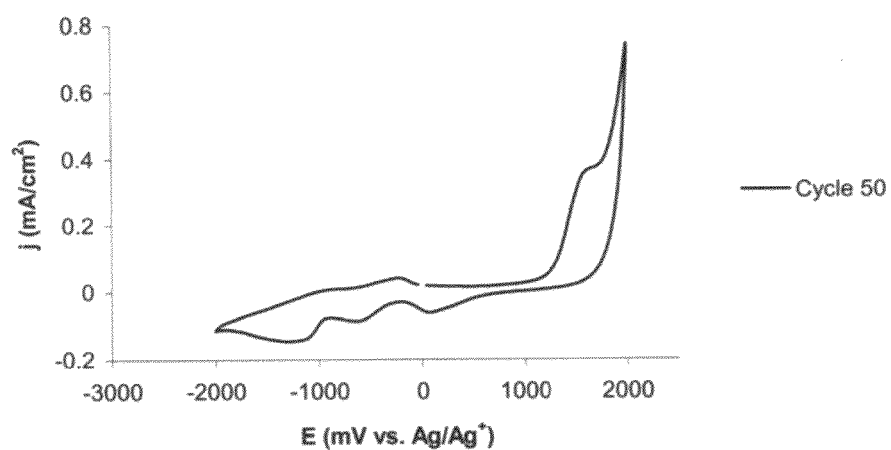

Cycling of the polymer films in monomer-free electrolyte solution yields the following results shown in FIGS. 4a-4e. First, during the initial cycles between 2.0 and −2.0 V. the material shows very little electroactivity at all. However, the voltammograms change significantly over the course of 50 cycles before eventually stabilizing. Initially, the polymer oxidation onset at 1200 mV is not accompanied by a peak that could be attributed to reduction of the polymer to the neutral state. The polymer oxidation gradually becomes more prominent with extended cycling, and a reductive current response centered at 200 mV gradually develops. At the same time, more prominent current responses at relatively negative potentials gradually become more intense. The negative current responses at −700 and −1300 mV are attributable to reduction of the neutral polymer to the n-doped state, while positive current responses at −800 and −200 mV are attributable to oxidation of the n-doped polymer to the neutral state. These n-doping processes are much more intense than those obtained from electropolymerization over the 0 to 2000 mV narrow potential window (FIGS. 1a-1e). Ion channels were established during deposition by cycling between the potentials necessary to both oxidize and reduce the polymer, allowing both anions and cations to move freely within the polymer and between the polymer and the electrolyte solution.

Figure 5A:
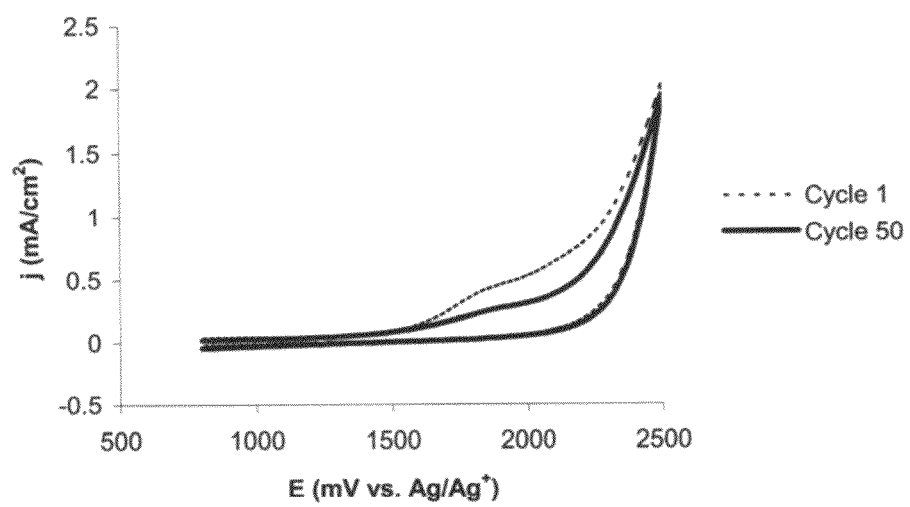
FIGS. 5a-5e are Voltammograms of poly(DTDMPy) films indicating that oxidation with an onset of 1200 and reduction centered at 200 mV are coupled, according to embodiments of the invention.
Figure 5B:
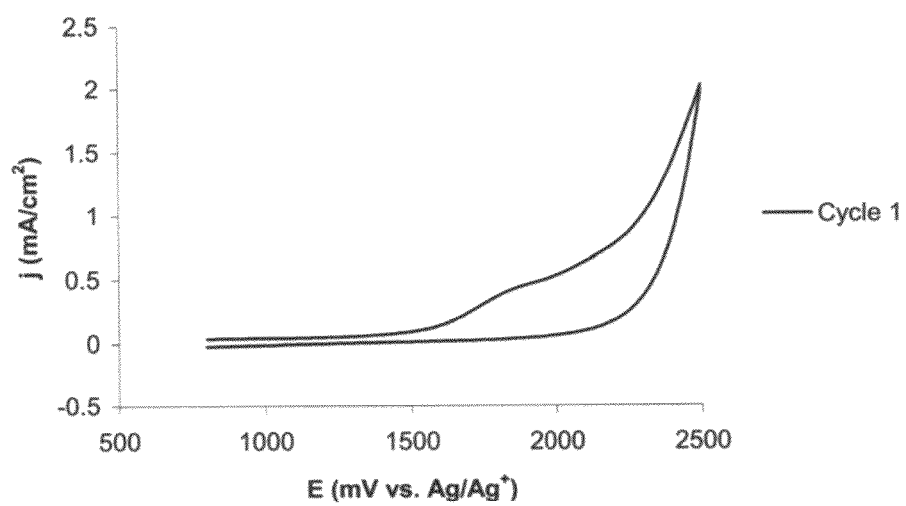
Figure 5C:
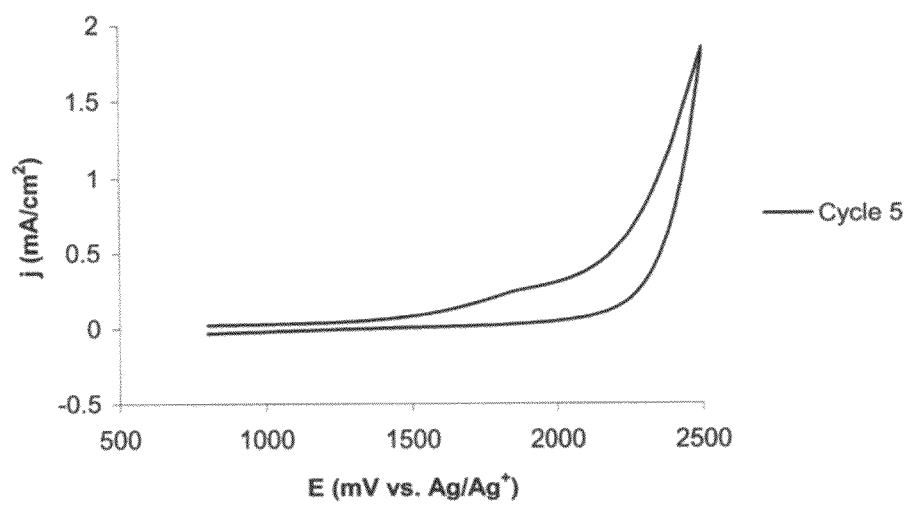
Figure 5D:
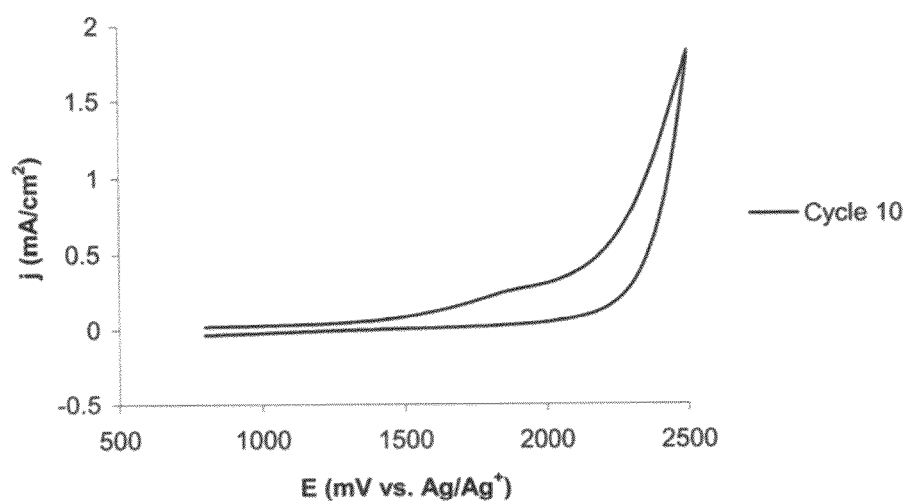
Figure 5E:
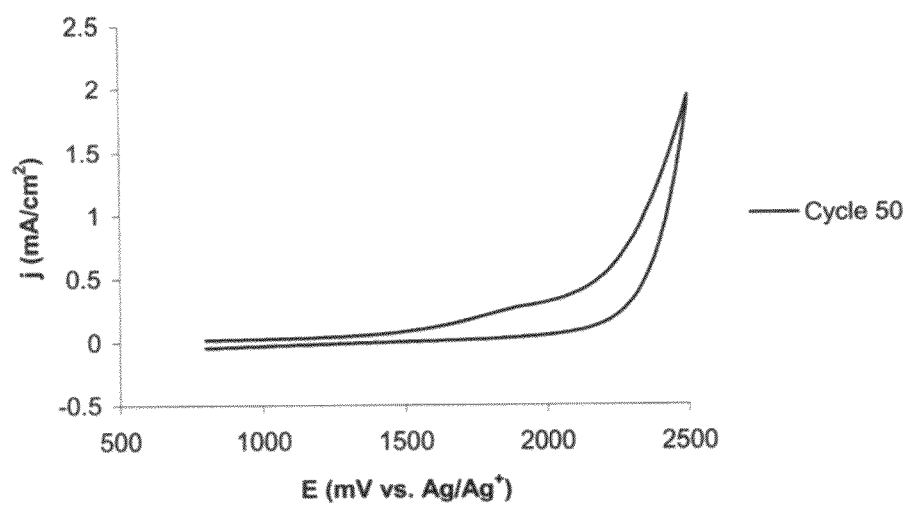

The changes in the voltammograms during extended cycling is thought to be a result of trapped counter ions present in the film. It is usually necessary therefore to first condition the polymer films with several potential scans in order to free trapped ions and permit ion migration. However, some ion trapping may occur even after extended cycling. With reference to FIGS. 5a-5e. the reduction observed at about 200 mV is coupled to the polymer oxidation shoulder. An initial potential scan from 800 to 2500 mV shows that the polymer film displays a shoulder on the solvent degradation signal that corresponds to polymer oxidation. This response. however, is not present on successive scans, indicating that the polymer has been oxidized and remained in its oxidized state throughout the experiment. Based upon the evidence that the two signals separated by about one volt are in fact coupled, it is inferred that ion-trapping is occurring.

While the present invention has been described in connection with what are currently considered to he the most prac-

What is claimed is:

1. A process for preparing a stable n-doping conjugated electroactive polymer comprising:

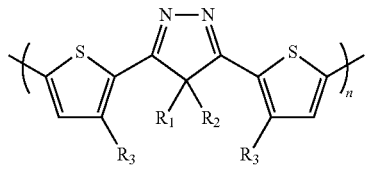

wherein R1 is selected from the group consisting of hydrogen; alkyl from 1 to about 22 carbon atoms; alkoxy from 1 to about 22 carbon atoms; nitro; halogen; cyano ester; mono- & di-alkylamine from 1 to about 22 carbon atoms; ester groups from 1 to about 22 carbon atoms; amide from 1 to 22 carbon atoms; alcohol from I to 22 carbon atoms; amino; sulphonate groups; silyl; perfluoro alky from 1 to about 22 carbon atoms;

wherein R2 is selected from the group consisting of: hydrogen; alkyl from 1 to about 22 carbon atoms; alkoxy from 1 to about 22 carbon atoms; nitro; halogen; cyano ester; mono- & di-alkylamine from 1 to about 22 carbon atoms; ester groups from 1 to about 22 carbon atoms; amide from 1 to 22 carbon atoms; alcohol from 1 to 22 carbon atoms; amino; sulphonate groups; silyl; perfluoro alky from 1 to about 22 carbon atoms;

wherein R3 is selected from the group consisting of: hydrogen; alkyl from 1 to about 22 carbon atoms; alkoxy from 1 to about 22 carbon atoms; nitro; halogen; cyano ester; mono- & di-alkylamine from 1 to about 22 carbon atoms; ester groups from 1 to about 22 carbon atoms; amide from 1 to 22 carbon atoms; alcohol from I to 22 carbon atoms; amino; sulphonate groups; silyl; perfluoro alky including from I to about 22 carbon atoms; and n is an integer between 2 and 200 providing a solution containing monomeric thiophene substituted 3,5-Dithien-2-yl-4,4-disubstituted pyrazole in tetramethylammonium tetrafluoroborate and acetonitrile;

contacting a platinum substrate with said solution;

selecting a first electrical potential necessary to oxidize thiophene substituted 3,5-Dithien-2-yl-4,4-disubstituted pyrazole and a second electrical potential necessary to reduce thiophene substituted 3,5-Dithien-2-yl-4,4-disubstituted pyrazole;

applying an electrical potential to said platinum substrate in contact with said solution;

cycling said electrical potential at a predetermined rate of change between said selected first electrical potential and said selected second electrical potential to effect electrodeposition of poly(thiophene substituted 3,5-Dithien-2-yl-4,4-disubstituted pyrazole) on said platinum substrate; and growing a film of stable n-doping poly(thiophene substituted 3,5-Dithien-2-yl-4,4-disubstituted pyrazole) of a desired thickness on said platinum substrate by cycling said electrical potential for a predetermined time.

2. The process according to claim 1, wherein R1 is alkyl from 1 to about 22 carbon atoms; R2 is alkyl from 1 to about 22 carbon atoms; R3 alkyl from 1 to about 22 carbon atoms.

3. The process according to claim 1, wherein said selected first electrical potential and said selected second electrical potential are about +2000 mV and −2000 mV, respectively, with respect to a neutral reference.

4. The process according to claim 1, wherein R1 is alkoxy from 1 to about 22 carbon atoms; R2 is alkoxy from 1 to about 22 carbon atoms; R3 alkoxy from 1 to about 22 carbon atoms.

5. The process according to claim 1, wherein R1 is nitro, halo, or cyanoester from 1 to about 22 carbon atoms; R2 is nitro halo, or cyanoester from 1 to about 22 carbon atoms; R3 is nitro halo, or cyanoester from 1 to about 22 carbon atoms.

6. The process according to claim 1, wherein R1 is mono or diamine, ester or amide from 1 to about 22 carbon atoms; R2 is mono or diamine, ester or amide from 1 to about 22 carbon atoms; R3 is mono or diamine, ester or amide from 1 to about 22 carbon atoms.

7. The process according to claim 1, wherein R1 is amino; R2 is amino; R3 is amino.

8. The process according to claim 1, wherein R1 is alkylsulfonate and perfluoro alkyl from 1 to about 22 carbon atoms; R2 is alkylsulfonate and perfluoro alkyl from 1 to about 22 carbon atoms; R3 alkylsulfonate and perfluoro alkyl from to about 22 carbon atoms.

9. The process according to claim 1, wherein R1 is hydrogen; R2 hydrogen; R3 is hydrogen.

* * * * *